(12) United States Patent
Decuypere et al.

(10) Patent No.: US 7,261,888 B1
(45) Date of Patent: Aug. 28, 2007

(54) COMBINED USE OF TRIGLYCERIDES CONTAINING MEDIUM CHAIN FATTY ACIDS AND EXOGENOUS LIPOLYTIC ENZYMES AS FEED SUPPLEMENTS

(75) Inventors: Jaak Decuypere, Kuurne (BE); Noël Dierick, Aalter (BE)

(73) Assignees: Aveve N.V. (BE); Vitamex N.V. (BE)

(*) Notice: Subject to any disclaimer, the term of this patent is extended or adjusted under 35 U.S.C. 154(b) by 321 days.

(21) Appl. No.: 10/009,235

(22) PCT Filed: Jun. 6, 2000

(86) PCT No.: PCT/EP00/05192

§ 371 (c)(1),
(2), (4) Date: Jun. 11, 2002

(87) PCT Pub. No.: WO00/74497

PCT Pub. Date: Dec. 14, 2000

(30) Foreign Application Priority Data

Jun. 7, 1999 (EP) .................................. 99870120

(51) Int. Cl.
*A61K 38/46* (2006.01)
(52) U.S. Cl. .................... 424/94.6; 426/53; 426/54; 435/198
(58) Field of Classification Search ............ 424/94.1, 424/94.2, 94.6; 426/2, 52, 53, 54, 608, 641; 435/197, 198
See application file for complete search history.

(56) References Cited

U.S. PATENT DOCUMENTS 3,477,853 A * 11/1969 Hull et al. ............... 426/35
3,857,968 A * 12/1974 Haas et al. ............... 426/33
4,944,944 A * 7/1990 Tang et al. .............. 424/94.6

FOREIGN PATENT DOCUMENTS

| EP | 0 429 879 | 6/1991 |
| EP | 0 600 439 | 6/1994 |
| GB | 1 442 093 | 7/1976 |
| JP | 54 080462 | 6/1979 |
| JP | 62 289152 | 12/1987 |

OTHER PUBLICATIONS http://classes.aces.uiuc.edu/AnSci308/HumanLact.html.*
Nars et al., Monatsschr Kinderheilkd. Apr. 1984;132(4):233-7.*
Salle et al. Arch Fr Pediatr. Oct. 1992;49(8):761.*
Melichar et al., Padiatr Padol. 1986;21(3):241-8.*
Suranyi et al., Gyermekgyogyaszat. Sep. 1959;10:257-66.*
Jack Odle, *Journal of Nutrition*, 127(6):1061-1067 (1997).

* cited by examiner

Primary Examiner—Irene Marx
(74) Attorney, Agent, or Firm—Howrey LLP

(57) ABSTRACT

The present invention relates to the use of triglycerides (TG) containing medium chain fatty acids (C4 to C12), combined with exogenous lipolytic enzymes (esterases or lipases) as a feed supplement for animals in order to prevent and/or alleviate the problems which are frequently met at this moment. This results in a marked improvement of the growth performances without the use of the classical, but contested, feed additives.

10 Claims, 4 Drawing Sheets

Fig. 1. In Vitro release of MCFA (g / 100g TG) at different pH's from the different triglycerides tested
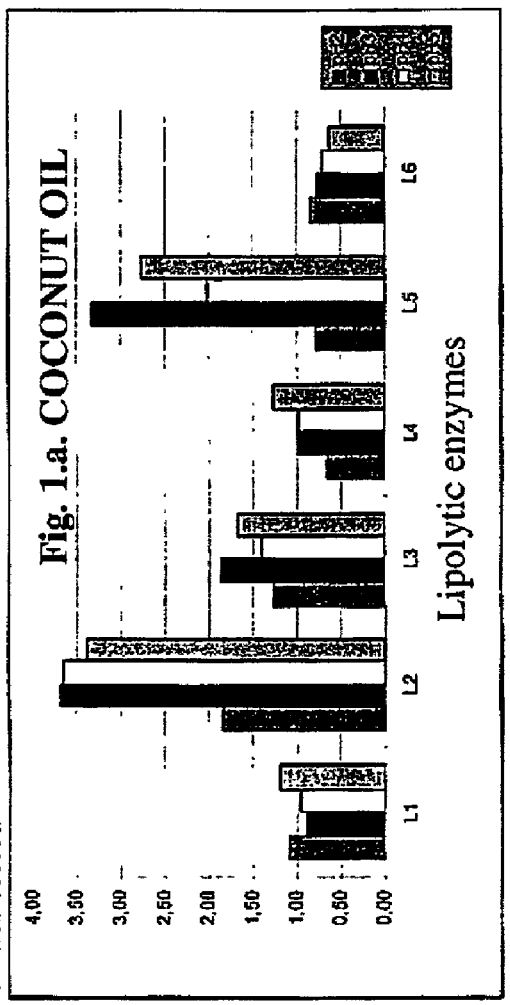
Fig. 1.a. COCONUT OIL
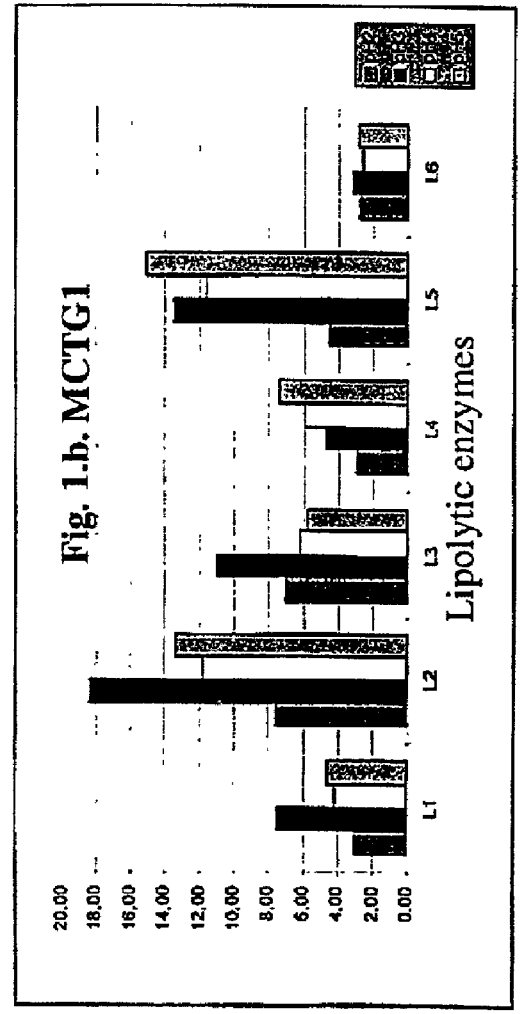
Fig. 1.b. MCTG1

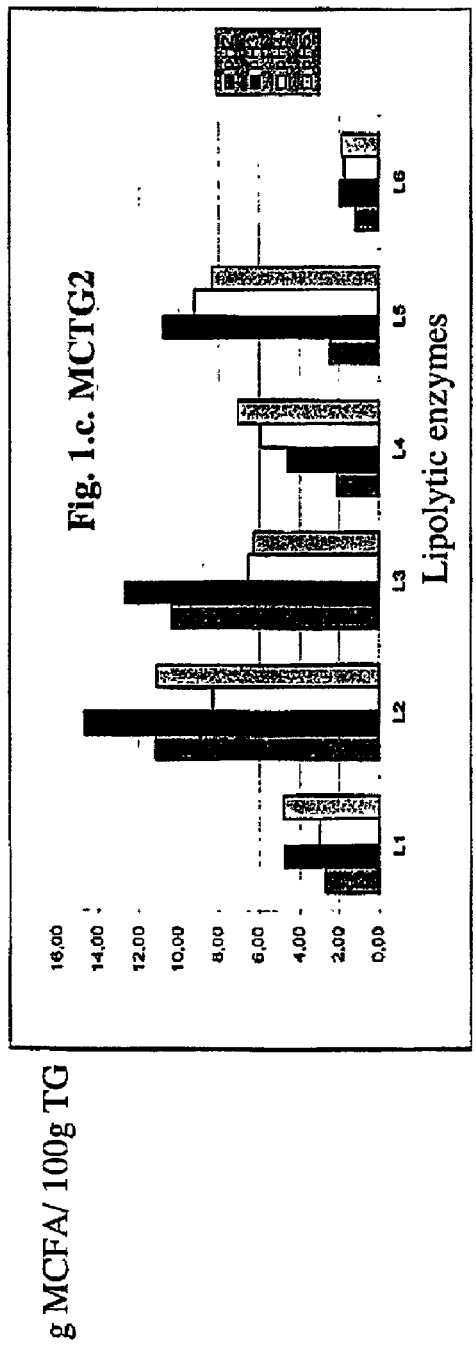
Fig. 1. (followed) In Vitro release of MCFA (g / 100g TG) at different pH's from the different triglycerides tested

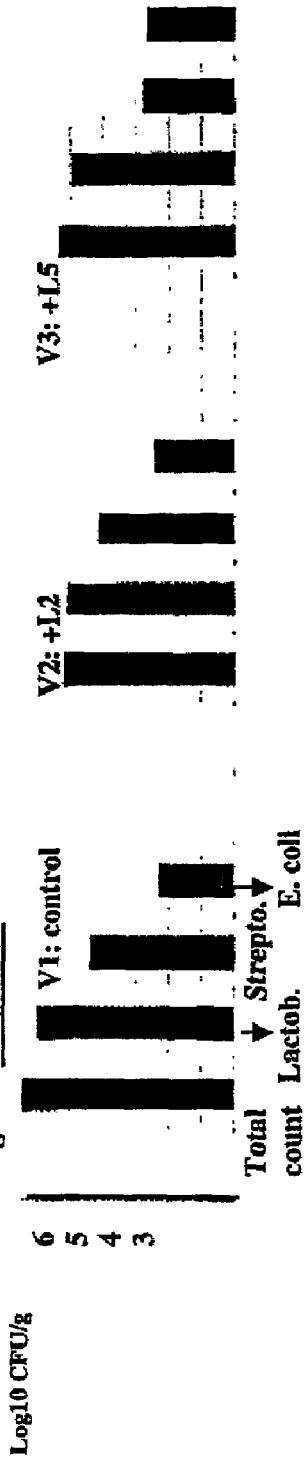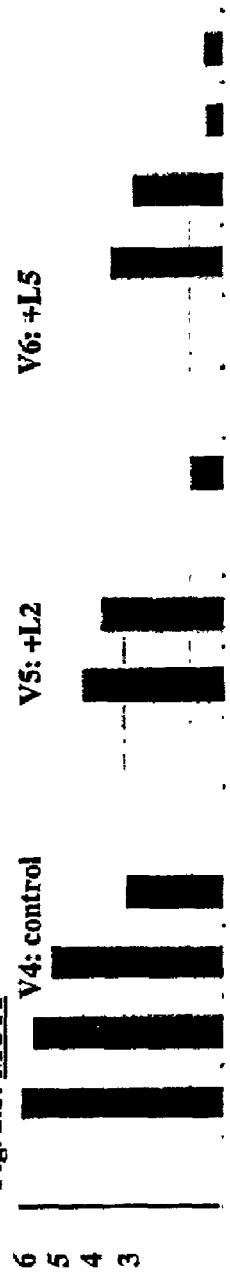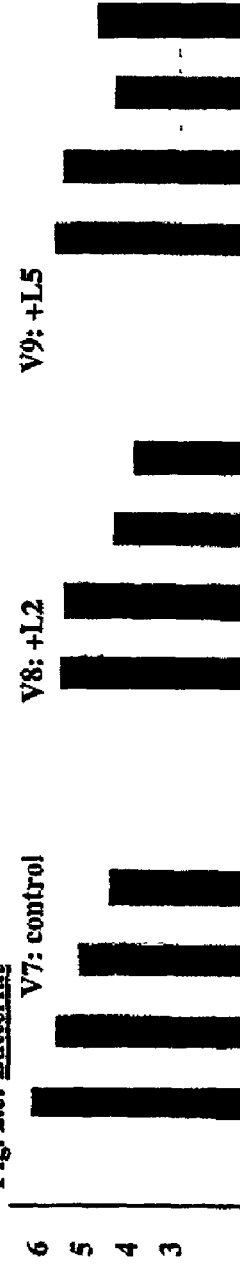
Fig. 2. In Vivo bacterial counts in the stomach contents of cannulated piglets fed three different TG and two lipases
Fig. 2.a: Coconut oil
Fig. 2.b: MCT1
Fig. 2.c: Butterfat

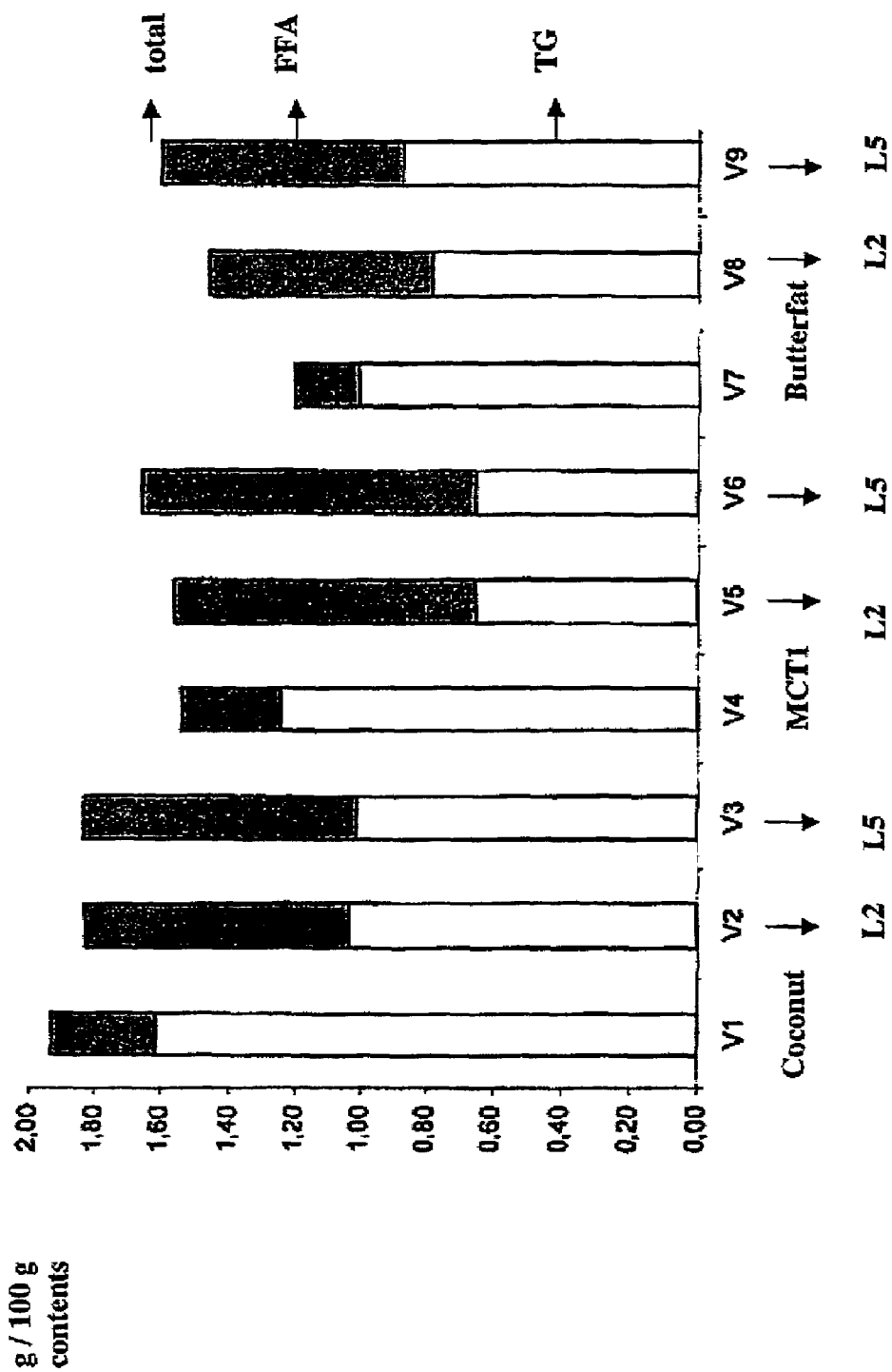
Fig. 3. In Vivo concentration of total, TG-bound and free fatty acids (FFA) in stomach contents of cannulated pigs fed three TG and two lipases

COMBINED USE OF TRIGLYCERIDES CONTAINING MEDIUM CHAIN FATTY ACIDS AND EXOGENOUS LIPOLYTIC ENZYMES AS FEED SUPPLEMENTS

This application is a §371 national stage filing of PCT/EP00/05192, filed 6 Jun. 2000 (published in English on 14 Dec. 2000 as WO 00/74497 A1) and claiming priority to EP 99870120.5 filed 7 Jun. 1999.

FIELD OF THE INVENTION

The present invention relates to the use of triglycerides (TG) containing medium chain fatty acids (MCFA; C4 to C12), combined with exogenous lipolytic enzymes (esterases or lipases) as a feed supplement for animals, especially early weaned pigs in order to prevent and/or alleviate the problems which are frequently met at this moment. This results in a marked improvement of the growth performances without the use of the classical, but contested, feed additives.

BACKGROUND OF THE INVENTION

Early weaning (3 to 4 weeks of age) of piglets has become a general practice in pig husbandry systems for increasing the productivity and maintaining the profitability. Early weaning, however, burdens the piglet with a lot of stresses, mainly of environmental, nutritional and immunological origin, combined with a more or less pronounced depression of feed intake and mobilization of body reserves. Maldigestion and malabsorption often aggravate the situation resulting in digestive upsets due to bacterial overgrowth and/or viral infections. These phenomena greatly interfere with the profitability of the enterprise. There is a vast body of literature covering these issues (e.g. VAN DER PEET, 1992; PARTRIDGE, 1993).

The currently used methods to handle those problems aim at the adaptation of the feed to the digestive capacity of the piglet, and/or by improving the acceptability of the feed by the use of specific ingredients (e.g. milk powder and derivates, such as whey and lactose, dried blood serum, flavors), all or not combined with an increase of the energy content of the feed. An increase of the energy content can be obtained among others by including easily digestible or metabolizable fats. The usefullness of medium chain triglycerides (MCTG) in this context is well documented both in neonatal (ODLE, 1999) and in weaned piglets (CERA et al., 1989). The reasons for the usefullness of MCTG is their specific digestive and metabolic fate, reviewed by BACH & BABAYAN. (1982).

Digestive upsets are prevented and/or treated by supplementing the feed with pharmaceutical antimicrobial substances (antibiotics, chemotherapeutics, called antibiotics further on). The combined effects of the above mentioned interventions mostly result in a pronounced improvement of the growth performances (called 'growth promotion' further on). This growth promotion is mainly due to, depending on the circumstances, an improved feed intake all or not combined with a better feed conversion (=kg feed/kg gain). However there is a growing concern about the use of antibiotics for growth promotion in animal production systems. Especially there is a well-considered fear for the risk of the emergence of cross-resistance to some last-resort antibiotics used in human medicine (CORPET, 1996; WEGENER et al., 1998). Therefore most of those antibiotics (so called growth promoters) are already or will be banned in the near future in the EU which justify an urgent need for alternatives.

Because there is a general belief that the digestive pathology in early weaned pig is mainly caused by Gram−bacteria (especially *E. coli*) and that Gram+lactic acid bacteria (Bifidobacteria, Lactobacilli) have a protective and/or antagonistic effect against them, the currently proposed alternatives are selected for their anti-*E. coli* activity: eg. cupper and zinc compounds, selected organic acids (short chain fatty acids (SCFA, formic, acetic-, propionic acid), lactic, fumaric-, citric, malic, sorbic acid), probiotics (mainly lactic acid bacteria) and/or prebiotics (mainly bifidogenic oligosaccharides, so called NDO's). Cu- and/or Zn-compounds are effective but are not acceptable because their effect on the environment (pollution). Results obtained with pro- and/or prebiotics are unpredictable and generally spoken disappointing (CHESSON, 1994).

Similar problems exist in other animal species and in animals of other age groups.

Only SCFA and the 'classical' organic acids are the most promising alternatives for the moment (ROTH et al., 1998). However rather high doses are needed, so that their usefullness is limited by the high cost, their corrosive nature and their averse taste which interferes greatly with the feed intake of the piglets The antimicrobial effects of fatty acids (FA) in general and their salts (soaps) is already know for decades. A reevaluation of the antimicrobial effects of selected FA (and derivates) is given in the review of KABARA (1978). Special attention was thereby given to lauric acid (C12, a member of the MCFA-family) and derivatives.

Further literature data lead to conclude the relative important contribution of MCFA in the milk-lipid of certain animal species (e.g. rabbit, goat, horse), while in other species the concentrations were low or even nihil as in sow's milk (DIERICK, 1998, literature compilation, personal communication). In most mammals there is a more or less pronounced preduodenal (=not of pancreatic origin) lipolytic activity originating from lingual or gastric secretions. The activity of those lipases is independent of the presence of colipase and bile acids, is active and stable in a broad range of pH's and has a preference for MCFA in milk fat. The preduodenal lipase activity is high in preruminant calves and rabbits, moderate in piglets and absent in poultry (MOREAU et al., 1988). An excess MCFA can have important side-effects: indeed, there are data that they can be hypnotic in new born pigs (ODLE, 1999), and are a strong stimulus for CCK, an intestinal hormone with a pronounced satiating activity what could interfere with the feed intake (LEPINE et al., 1989). A lower feed intake could also be the result of the strong (goat-like) odour and averse taste of free MCFA, although data in this context are scarce and non-conclusive.

SUMMARY OF THE INVENTION

The present invention aims at providing new feed supplements for animal feeds, particularly for early weaned pigs which can replace the commonly used (and contested) antibiotics and other growth enhancers.

The present invention is related to a feed supplement or feed composition whereby the feed supplement is a premix of feed additives (vitamins, minerals, antibiotics, among others) with a carrier for use as part (mostly 1 to 5%) of a complete food, and whereby the feed composition is the entire listing of the different feed ingredients used in a complete feed: an other term often used is "feed formula".

The present invention provides the use of at least one triglyceride (TG) containing medium chain fatty acids (MCFA: C4 to C12), combined with at least one exogenous lipolytic enzyme (esterase or lipase) as a feed supplement for animal feeds, especially for early weaned pigs in order to prevent and/or alleviate feeding problems which are frequently met at this moment. The addition of this combination of TG and exogenous lipolytic enzymes to feed surprisingly results in a physiological environment in the stomach which regulates and stabilizes the gastrointestinal microflora. This effect, combined with the fact that an easily digestible and metabolizable source of energy is provided, surprisingly results in a marked improvement of the growth which is comparable with the growth promotion obtained with the commonly used (and contested) antibiotics and other growth enhancers without negative side effects for the animal, the feed industry and the consumer.

BRIEF DESCRIPTION OF THE DRAWINGS

FIG. 1 relates to the results obtained in example 1 and presents the in vitro released MCFA (expressed as g/100 g TG) for the different examined TG's (FIG. 1.*a*. coconut oil, FIG. 1.*b*. MCTG1, FIG. 1.*c*. MCTG2, FIG. 1.*d*. butterfat) and selected enzymes. The enzymes, coded L1 to L6, were used in a dose of 10.000 ppm on the basis of TG. The release of FA was studied in buffered medium at pH 2, 3, 4 and 5 as being representative for the pH conditions prevailing in vivo in the stomach.

FIG. 2. relates to the results obtained in example 2 and presents the total and selective bacterial counts (expressed as $\log_{10}$ Colony Forming Units, CFU per g fresh contents )in the stomach contents of cannulated pigs. FIG. 2.*a*, 2.*b*. and 2.*c*. give the results for the feeds with 5% coconut oil, MCTG1 and butterfat respectively. The first component of each figure presents the results obtained without lipolytic enzymes, the second and third block, the results with the addition of L2 and L5 (1000 ppm on feed basis) respectively. The first bar is the total count, the following bars are the number of lactobacilli, streptococci and *E. coli*. The results indicate that with each TG, the enzymes cause a reduction of the total count and the number of lactobacilli.

FIG. 3 relates to the results of the analysis of the fat fractions in the gastric contents (in g/100 g contents) of the cannulated pigs used in example 2. The proportion of free FA to total FA is given for the feeds with the different TG's used without enzyme (V1: coconut oil, V4: MCTG1; V7: butterfat) or with the supplementation of L2 or L5 (1000 ppm on feed basis). The free FA released without enzymes result from the activity of the endogenous preduodenal lipases. The results indicate that the lipolytic enzymes used grealty enhance the release of free FA from each TG tested.

DETAILED DESCRIPTION OF THE INVENTION

The present invention relates to the use of at least one triglyceride (TG) containing medium chain fatty acids (MCFA), combined with at least one exogenous lipolytic enzyme (esterase or lipase) as a feed supplement for animal feeds in order to prevent and/or alleviate the problems which are frequently met at this moment.

The present invention thus also relates to a feed supplement composition which comprises at least one triglyceride (TG) containing medium chain fatty acids (MCFA) and at least one exogenous lipolytic enzyme (esterase or lipase).

Medium chain fatty acids according to the present invention include both even and odd fatty acids, such as fatty acids containing C4 (butyric acid, butanoic acid), C5 (valeric acid), C6 (caproic acid, hexanoic acid), C7 (heptanoic acid), C8 (caprylic acid, octanoic acid), C9 (pelargonic acid), C10 (capric acid, decanoic acid), C11 (undecanoic acid) or C12 (lauric acid, dodecanoic acid). The MCFA triglyceride component according to the present invention may be a naturally occuring triglycerides containing composition, such as butterfat and coconut oil. Alternatively, said triglyceride component may comprise one or more industrially prepared triglycerides or a mixture of naturally occuring and industrially prepared triglycerides. Said triglyceride may be prepared by interesterification of C4 to C12 chain fatty acids.

Examples of naturally occurring substances which are rich in medium chain fatty acid containing triglycerides include but are not limited to coconut oil, palm kernel oil, babassu oil, cohune oil, tacum oil, cuphea oil derived from plant seeds, milk of mammalian species, such as milk from horse, rat, goat and rabbit, or butterfat.

Examples of commercial sources of chemically synthesized structured or tailor-made triglycerides containing medium chain fatty acid include but are not limited to those given in Table 10 or those exemplified in the Materials section of the Examples.

The lipolytic enzyme component according to the present invention may comprise a lipase or an esterase, a mixture of lipases or a mixture of esterases or a mixture of lipases and esterase. Said lipases or esterases may be naturally occuring or industrially prepared. Said lipolytic enzymes may be from microbial, mammalian or plant origin.

Examples of commercially available plant lipases include but are not limited to lipases from wheat, castor bean, rape, mustard and lupin.

Examples of commercially available microbial lipases include but are not limited to the lipases as given in Table 11 or those exemplified in the Materials section of the Examples.

Examples of commercially available esterases include but are not limited to pregastric esterase (PGE) from sublingual tissue of calf, kid and lamb, rennet paste from engorged abomasa of calf, kid and lamb, esterase from rabbit liver or porcine liver.

The triglyceride component according to the invention as defined above is added in a concentration of about 0.05% to about 20% to the feed. Preferably said triglyceride component according to the invention as defined above is added in a concentration of about 0.25% to about 10% to the feed.

Preferably said lipolytic enzyme component is added in a concentration of about 100 to about 10,000 ppm to the feed.

The use of a feed supplement composition according to the present invention is preferably as a feed supplement for animal feeds, particularly for early weaned pigs. The use of the feed supplement compositions according to the present invention do not, however, exclude the use of such compositions as a feed supplement for pigs of other age categories or as a feed supplement for other types of animals.

The present invention also relates to the use of a combination of at least one MCFA TG and at least one lypolytic enzyme according to the present invention for the preparation of a feed supplement preferably for early weaned piglets.

The present invention also relates to methods for the preparation of feed supplements according to the present invention comprising the step of mixing together of different MCFA TG and lipolytic enzyme components according to the invention.

The mechanism by which SCFA, MCFA and other organic acids excert antimicrobial activities is well documented in the literature. The current belief is that undissociated (RCOOH=non ionized) acids are lipid-permeable and in this way can pass across the microbial cell membrane and dissociate (RCOOH→RCOO$^-$+H$^+$) in the more alkaline interior of the microorganism. This brings about an acidification of the intracellular pH below permissible levels for survival. In other words organic acids act as protonophores that increase the inward leak of H$^+$ so that efflux is not rapid enough to alkalinize the cytoplasm again. The physicochemical characteristics of the organic acids greatly influence their ability to act as protonophores: (molecular weight, pKa (dissociation constant), solubility). The physiological environment in which they are present (especially the pH in the different locations of the gastrointestinal tract) is also a very important factor. Further, the type of the microbial envelope (mainly peptidoglycan in Gram+, and lipopolysaccharide in Gram−bacteria) greatly influences the passage of the acids through the membrane.

First, In preliminary in vitro experiments, in which a broad range of organic acids (SCFA, MCFA and other commonly used organic acids in the feed and food industry) were tested for their antibacterial activity against the dominant bacteria of the small intestinal microflora, the present inventors unexpectedly found that the SCFA and the commonly used organic acids only were bacteriostatic at higher concentrations (0.02 to 0.04 M) for the Gram−flora (and to a lesser extent for Streptococci). However, with the MCFA an unexpectedly high bacteriostatic and bactericidal activity was found against both Gram+ and Gram−bacteria. The antibacterial activity was pH dependent and highest at lower pH, thus when a relatively high proportion of the FA was in the undissociated form. In the same experiments a temptative minimal bacteriocidal concentration of 0.005 to 0.01 M was put forward.

Also unexpected was that by using a combination of MCFA, the antibacterial spectrum of the antibiotic growth promotors used in the intensive animal production could be mimicked totally.

The specific characteristics of MCTG as an easily available energy source are well documented. Their beneficial effect can be summarized as follow (BACH & BABAYAN, 1982):

MCTG are digested, absorbed and transported rapidly in disorders were digestion and absorption are not optimal. Maldigestion and malabsorption are frequently observed in newly weaned piglets, and are attributed to a sharp drop in the activity of most of the digestive enzymes. The deficiency of lipolytic enzymes shortly after weaning is very pronounced.

MCTG are oxidized rapidly in the organism and are a source of abundant and rapidly available energy. However MCTG are ketogenic, what, when high doses are given, can have narcotic side effects. This side effect is certainly undesirable in piglets.

Also the depressive effect on the voluntary feed intake, by activation of CCK, is unwanted. Also unwanted (by the producer and/or the animal) is the strong unpleasant odour of the free MCFA which evaporate relatively easily.

In order to obtain the positive effects and to avoid the negative characteristics of MCFA, the inventors had the original idea to use a combination of a TG, containing sufficient MCFA, together with a lipolytic enzyme as a feed supplement, with the intention that sufficient MCFA should be released in the stomach to have a sterilizing effect, resulting in a lesser bacterial load in the small intestine and to prevent digestive upsets. This effect, combined with the extra easily available energy of the MCFA, and the supplementation of the natural lipase activity in the stomach and upper intestine by the exogenous lipolytic enzyme(s), resulted unexepectedly in a growth promotion making the use of antibiotics unnecessary. The expected gradual release and absorption of the free MCFA unexpectedly avoided the unwanted side effects.

In summary the invention describes the composition of a natural growth promoting feed supplement for the use in animals.

The following examples and drawings merely serve to illustrate the present invention and are not meant to be limiting in any manner.

EXAMPLES

Materials

By way of example: the following fats (TG) were chosen to illustrate the present invention: butterfat, coconut oil, and two commercially available sources of MCTG: MCTG1 (Aldo MCT Kosher Food Grade) and MCTG2 (Stabilox-860), commercialized by LONZA Inc. (Fair Lawn, N.J. 070410, USA) and LODERS-CROKLAAN BV (NL-1521 AZ Wormerveer) respectively. By way of example the following lipolytic enzymes were chosen to illustrate the present invention: L1: Lipozyme 10.000L, NOVO Nordisk A/S, 2880 Bagsvaerd, Denmark; L2: Lipase 10.000P, Biocatalysts Ltd., CF37 5UT Pontypridd, Wales, UK; L3: TP 516P, Biocatalysts Ltd., CF37 5UT Pontypridd, Wales, UK; L4: LIPOMOD 224P, Biocatalysts Ltd., CF37 5UT Pontypridd, Wales, UK; L5: Lipase SAIKEN, NAGASE & Co, Chuo-ku, 103 Tokyo, Japan; L6: Lipase ITALASE C, SBI, Systems Bio-Industries, Inc., WI 53187-1609 Waukesha, USA. The codes L1 to L6 will be used further on. The selection of TG and lipolytic enzymes described in these examples does not exclude the potential usefullness of other TG and lipolytic enzymes and combinations of them for the purposes described in this invention.

Methods for Extraction and Analysis of Different Lipid Compounds

A lipid extraction procedure using hexane/iso-propanol (3/2, v/v) avoiding any solvent evaporation step to prevent any loss of MCFA due to their great volatility was used.

Acid (H2SO4) catalyzed esterification of FA in the same extraction medium with formation of isopropyl esters (FAIPE) without loss of shorter esters or alteration of polyunsaturated higher FA was used. FAIPE appear in the upper hexane phase.

For the calculation of the concentration, quantitative capillary column (DB-225, 30 m, ID 0,25 mm, Film 0,25 μm) GLC chromatography of individual FAIPE using 2 internal standards (C9 used for C4 to C12 acids and C17 used for C14 to C18:3 acids) was used. Coefficients of variation on the response factors amounted to 0,94% for C9 and 2,51% for C17.

Individual free FA was extracted from the lipid extract with a strong anion exchange resin Amberlyst 26 before esterification in the same medium and analysed by capillary GLC mean recovery of added free FA amounted to 101, 9%.

Example 1

In Vitro Screening of MCFA Containing TG's and Lipolytic Enzymes for Lipolysis at Different pH's (Simulation of Gastric Conditions)

A selection of lipolytic enzymes to be tested, coded L1 to L6, was made which was based on their commercial availability and feasable price in commercial settings. MCFA containing TG's were selected on the basis of their specific MCFA content in the fat as specified in table 1.

TABLE 1

MCFA concentration (g/100 g FA) in the selected TG's

|  | C4 | C6 | C8 | C10 | C12 |
|---|---|---|---|---|---|
| Butterfat | 3.4 | 2.1 | 1.2 | 2.6 | 3.0 |
| Coconut oil | 0 | 0.7 | 8.5 | 6.2 | 48.8 |
| MCTG 1 | 0 | 2.8 | 69.1 | 27.7 | 0.4 |
| MCTG 2 | 0 | 0.2 | 57.5 | 42.3 | 0.0 |

The in vitro incubations were done in buffered circumstances at different pH's; a glycine buffer was used for incubations at pH 2 and pH 3; an acetate buffer was used for incubations at pH 4 and pH 5. Incubations were done for 180 min at 37° C. in a shaking water bath. The parameters used for the incubations were chosen in order to simulate as closely as possible the in vivo conditions in gastric contents. The medium used for the incubations was made up of the following ingredients: 0.250 g of the selected TG+2.250 g of a synthetic feed (based on starch, dextrose, casein and a vitamin-mineral premix)+10 ml buffer solution+0.5 ml pepsine solution (50 mg in 100 ml aqua dest)+10000 mg/kg fat (=ppm) of the selected commercial lipolytic enzyme preparation. If necessary the fat was molten, otherwise there were no special preparations (dispersion or emulgation) of the fat.

The results of the incubations are given in FIGS. 1a to 1d which presents the released MCFA in g/100 g TG for the different examined TG's. The hydrolytic activity was highest at pH 3 to 5 with each of the enzymes, which fits well with the pH normally occurring IN VIVO in the stomach of pigs. The amount of released free MCFA seems to be dependent on the amount present in the original source of TG. The amount of MCFA released was ±3.5% with coconut oil, 10-15% with the two MCTG's and ±0.5% with butterfat.

Example 2

In Vivo Experiment with Gastric Cannulated Pigs for the Study of the Release In Situ of MCFA by Endogenous and Exogenous Lipolytic Enzymes Three pigs (Belgian Landrace, stress negative, female) with an initial weight of ±8.5 kg were prepared with a gastric cannula using the technique of DECUYPERE et al. (1977). The cannulae were placed midway the curvatura major in the fundic region.

Three TG's (coconut oil, MCTG1 and butterfat, each) and 2 lipases (L2 and L5) were selected for the present experiment Nine feeds were prepared using 95% of a commercial feed for piglets with 5% of the selected (eventually molten) TG's all or not supplemented with the selected lipases (see Table 2 for the codes used further on). The fats were simply poured on the meal and thoroughly mixed in a horizontal mixer. The concentration of the lipases was 1000 ppm of the commercial preparation in the feed

TABLE 2

Feeds used in experiment 2

Coconut oil:

V1: 95% piglet feed + 5% coconut oil
V2: idem + 1000 ppm L2
V3: idem + 1000 ppm L5

MCTG1:

V4: 95% piglet feed + 5% MCTG1
V5: idem + 1000 ppm L2
V6: idem + 1000 ppm L5

Butterfat:

V7: 95% piglet feed + 5% butterfat
V8: idem + 1000 ppm L2
V9: idem + 1000 ppm L5

The composition of the piglet feed was based on maize, barley, dried acid whey, cassave, herringmeal, soybean oil, and was supplemented with a vitamin-mineral premix. The feed contained no growth promoting supplements. The proximate analysis of the feeds (V1, V4 and V7) in % of as given was: DM: 90.6, 90.7 and 90.8; total ash: 7.8, 7.9 and 8.5; crude protein: 15.1, 15.4 and 14.8; crude fat: 8.5, 8.3 and 8.3.

The feed was given dry, in three equal meals (9, 13 and 17 h), at 85% of the ad libitum intake of pigs with a comparable weight.

The experiment had a 3×3 Latin square design.

The experiment had a successful course. There were no health problems nor feed refusals. Statistics were done using ANOVA (1997), differences were at $p<0.01$ to $p<0.05$ (**) or $p<0.1$ (*)

Sampling of the gastric contents for the chemical analysis was done on 2 consecutive days, 2 times a day, 30 min after the 9 h and 13 h meal. The pH was measured directly, thereafter the samples were stored at −20° C. till further analysis.

The sampling of the gastric contents for the bacteriological analysis was done during 1 day, 90 min after the 9 and 13 h meal. The bacterial counts were done using the technique of VAN DER HEYDE et al. (1964). The media (all from OXOID, UK) used were RCM agar+hemin for the total count (48 h, anaerobic), Rogosa agar for the Lactobacilli (48 h, anaerobic), Slanetz & Bartley agar for the fecal Streptococci (24 h, aerobic), and EMB agar for E. coli (24 h, aerobic). All incubations were at 37° C. Results are expressed as $\log_{10}$ CFU/g fresh contents (colony forming units)

The results of the experiment can be summarized as follows:

The pH of the stomach contents measured 30 and 90 min after feeding did not differ between the treatments (feeds) and ranged between 4.2 and 5.01. This is within the optimum range for the lipolytic activity of L2 and L5 as was found in the first experiment.

The results of the bacteriological counts are presented in table 3 and in FIG. 2.

TABLE 3

Bacteriological counts in the gastric contents of the piglets fed diets 1 to 9 ($\log_{10}$ CFU/g fresh contents: mean ± s.d) (n = 6).

|  | Total | Lacto. | Strepto. | E. coli |
|---|---|---|---|---|
| Coconut oil | | | | |
| V1 | 6.4 ± 0.8 | 6.0 ± 0.8 | 4.3 ± 1.0 | 2.3 ± 1.2 |
| V2 | 5.2 ± 0.3** | 5.0 ± 0.3** | 4.1 ± 0.6 | 2.4 ± 1.4 |
| V3 | 5.3 ± 0.6** | 4.9 ± 0.7** | 2.7 ± 1.6* | 2.6 ± 2.1 |
| MCTG1 | | | | |
| V4 | 6.1 ± 0.2 | 5.7 ± 0.5 | 5.2 ± 0.4 | 2.9 ± 1.6 |
| V5 | 4.2 ± 0.5** | 3.7 ± 0.5** | 0.0** | 1.0 ± 1.5** |
| V6 | 3.4 ± 1.7** | 2.7 ± 1.4** | 0.5 ± 1.2** | 0.5 ± 1.2** |
| Butterfat | | | | |
| V7 | 6.4 ± 0.4 | 5.7 ± 0.8 | 5.0 ± 0.6 | 4.1 ± 0.5 |
| V8 | 5.6 ± 0.9* | 5.5 ± 0.3 | 4.0 ± 0.7* | 3.4 ± 0.1* |
| V9 | 5.7 ± 0.5* | 5.5 ± 0.5 | 4.0 ± 0.7* | 4.5 ± 1.4 |

*, **: differences per TG within the column

The most important results are:

with coconut oil, both L2 and L5 reduced 10 fold the total count and the number of lactobacilli with MCTG1, both enzymes had a very pronounced (mostly p<0.001) effect and reduced the total count and the lactobacilli by a factor 100 to 1000; streptococci and E. coli were mostly reduced to non detectable levels with butterfat, there was a 10 fold reduction of the total count and the number of streptococci.

The results allow the conclusion that the combination of a MCFA containing TG and a lipolytic enzyme in the feed is able to suppress the total bacterial count and the dominant flora. This effect most likely is due to the release of free MCFA from the TG's used.

This statement was confirmed by the chemical analysis of the different fat fractions in the gastric contents collected during present experiment. The results of the analysis are given in FIG. 3 in which the amount of total and free FA per 100 g fresh gastric contents are presented.

The results expressed as g free FA per 100 g total FA in the stomach contents, or in other words the degree (%) of hydrolysis of the TG, is given in table 4.

TABLE 4

Degree of hydrolysis (g free FA/100 g total FA in fresh gastric contents) of the different TG's used in present experiment as influenced by L2 or L5

|  | control | +L2 | +L5 |
|---|---|---|---|
| Coconut oil | V1 | V2 | V3 |
|  | 16.5 | 43.2 | 44.8 |
| MCTG1 | V4 | V5 | V6 |
|  | 18.9 | 58.5 | 60.9 |
| Butterfat | V7 | V8 | V9 |
|  | 16.8 | 46.8 | 45.8 |

The results for the individual FA (not given here) indicated that there was no preferential release of specific FA; in other words the release of individual FA is roughly proportional to their content in the TG used. Out of the results presented in FIG. 3 and table 1 it can be concluded that the endogenous lipolytic activity in the stomach of the piglets hydrolyses±16-19% of the TG. The addition of the exogenous lipolytic enzymes increases the hydrolysis about threefold.

It is striking and unexpected that the release of MCFA runs parallel with the degree of suppression of the bacterial load in the stomach: the most efficient suppression was observed with the combination MCTG1+L5, which caused 60.9% hydrolysis of the TG in the stomach (corresponding with a concentration of ±1% of free FA and 0.6% of MCFA), followed by coconut oil+L5 (0.8% FA acids and 0.3% MCFA) and butterfat+L5 (0.8% free FA and 0.06% MCFA).

Example 3

Zootechnical Experiment in Commercial Settings: Growth Performance Combined with Ex Vivo Observations on the Gastric Contents The aim of this experiment was to check if the above mentioned concept was applicable and suitable in commercial settings and to check, when a growth promotion was obtained, this was comparable with the growth promotion obtained in early weaned piglets with antibiotics or a combination of organic acids with proven effectiveness.

For this experiment 244 freshly weaned piglets (Seghers Hybrid F1, initial w eight±6.5 kg) were divided according to litter, sex and weight in 4 groups: A: 68; B=61; C=60 and D=55 piglets. The experiment was run in commercial settings in temperature controlled facilities.

The composition of the feeds used was based on barley, wheat, maize flakes, extruded maize, extruded soybeans, soy-flour, herring meal, 2.5% TG, and a commercial premix (mainly based on milk products, vitamins+minerals) for early weaned piglets (12.5%). The treatments (A to D) differed in the used TG's and the used additives (see table 5). The feeds contained no growth promoting antibiotics. Feed A was a negative control, feed D a positive control containing a mix of commonly used organic acids The calculated proximate analysis of the feeds used was equalized. The formulated contents were (% fresh): DM: 90.0 à 88.8, crude protein: 18.7 à 18.9, crude fat 6.9, total ash: 5.1-5.3 The energy content was (Nef97), 2463-2475 kcal/kg, the ileal digestible amino acids were set at: Lys: 1.07%, Met+Cys: 0.65, Thre: 0.66, Try 0.19.

TABLE 5

Treatments used in the zootechnical experiment

| Treatment | A | B | C | D |
|---|---|---|---|---|
| TG (2.5%) | soybean oil | MCTG2* | MCTG2 | soybean oil |
| Lipase (L5) | — | — | 1000 ppm** | — |
| Supplement organic acids*** | — | — | — | 1.5% |

*MCTG2 was selected upon commercial availability
**based on fresh feed
***0.25% citric acid + 0.75% fumaric acid, 0.5% Na-formiate (as specified by the feed manufacturer)

The feed was prepared by a commercial feed company wich used a spray-equipment for fats and other liquid supplements. The feed was offered dry, ad libitum; water was continuously available via a nipple.

The experiment lasted 3 weeks. The piglets were weighed individually at the start of the experiment and weekly thereafter; feed intake was recorded daily per two pens point feed hopper for two pens with ±15 piglets each). Therefore statistics only could be done for the weights. The visual health condition of the pigs per pen was checked daily and coded on a scale from 0 (extremely bad) to 10 (excellent).

The zootechnical results on a weekly basis are presented in table 6

TABLE 6

Zootechnical performances of the piglets as influenced by the treatments (mean ± s.d.)

| Treatment | week 1 | week 2 | week 3 | week 1 to 3 | % of control |
|---|---|---|---|---|---|
| Feed intake (g/d) | | | | | |
| Feed A | 156 | 365 | 472 | 331 | 100 |
| Feed B | 191 | 376 | 536 | 368 | 111 |
| Feed C | 180 | 391 | 533 | 361 | 110 |
| Feed D | 189 | 355 | 469 | 338 | 102 |
| Daily growth (g/d) | | | | | |
| Feed A | 127 ± 57 | 127 ± 57 | 300 ± 133 | 185 ± 81 | 100 |
| Feed B | 164 ± 73** | 160 ± 70** | 301 ± 144 | 208 ± 95* | 112 |
| Feed C | 165 ± 90** | 161 ± 88** | 297 ± 173 | 207 ± 116* | 111 |
| Feed D | 141 ± 81** | 123 ± 73 | 280 ± 111 | 181 ± 71 | 98 |
| Feed conversion (kg feed/kg growth) | | | | | |
| Feed A | 1.23 | 2.88 | 1.57 | 1.79 | 100 |
| Feed B | 1.16 | 2.35 | 1.78 | 1.77 | 99 |
| Feed C | 1.09 | 2.43 | 1.79 | 1.74 | 97 |
| Feed D | 1.34 | 2.89 | 1.68 | 1.87 | 104 |

The visual health score (not given in detail) ranged between 4 and 9 on treatment A; for the other treatments the range was 8 à 9 without marked differences.

The daily growth did not differ between treatment A and D and between B and C. The most pronounced differences were obtained in the first two weeks after weaning during which the best growth performance (plus ±30% over the control) was obtained with treatment B and C. The better results obtained with the feeds B and C (MCTG2 without or with lipase) are due to an increase of the feed intake. The best feed conversion however was obtained with the feed containing MCTG2+lipase. The improvement of the growth using a combination of a MCFA TG (MCTG2) and a lipase was in the same range as obtained with quinoxalines (additives with both a Gram+ and Gram−spectrum) (Decuypere, meta analysis of literature data, unpublished results)

Two weeks after weaning 5 barrows of each experimental group were euthanized. Because the pigs were fed ad lib. there was no control of the feed intake. After dissection of the gastrointestinal tract, samples were taken from the stomach, and the upper (duodenum) small intestine. The samples were analysed chemically and bacteriologically in the same way as explained in the previous experiment. Only the total anaerobic count is reported here.

The pH of the gastric contents was ±3.5, and ±5.7 in the duodenum; there were no differences between the treatments. The total anaerobic counts are reported in table 7.

TABLE 7

Total anaerobic count ($\log_{10}$ CFU/g fresh contents, ± s.d.) in the stomach and upper small intestine in piglets, 2 weeks after weaning as influenced by the different treatments. (n = 5)

| Treatment | stomach | duodenum |
|---|---|---|
| A | 7.0 ± 0.2 | 6.4 ± 0.5 |
| B | 7.0 ± 0.2 | 6.1 ± 0.8 |
| C | 5.9 ± 0.5** | 5.6 ± 0.5** |
| D | 6.9 ± 0.2 | 5.9 ± 0.4 |

The results indicate that the feed with the combination of MCFA TG (MCTG2) and lipase (L5) caused a significant ±10 fold suppression of the bacteriological load, both in the stomach and upper intestine. That the effect was somewhat lower than in the previous experiment with the gastric cannulated pigs could be due to the lower amount of MCTG used in present experiment (2.5% versus 5%) and/or the different feeding and sampling procedures. Nevertheless, the present experiment confirmed the results obtained in the cannulated pig reported in example 3. The same can be stated for the results of the analysis of the different fat fractions (g/100 g fresh contents) and the degree of hydrolysis (g free FA/100 g total FA) in the gastric contents which are given in table 8

TABLE 8

Concentrations of free FA and total FA in gastric contents (g/100 g fresh contents, mean ± s.d.) and degree of hydrolysis (free FA/total FA in %) as influenced by the treatments in pigs two weaks after weaning (n = 5)

| Treatment | A | B | C | D |
|---|---|---|---|---|
| Free FA | 0.28 ± 0.06 | 0.44 ± 0.10 | 0.95 ± 0.22 | 0.31 ± 0.09 |
| Total FA | 1.05 ± 0.08 | 1.25 ± 0.22 | 1.35 ± 0.28 | 1.07 ± 0.17 |
| % hydrolysis | 26.7 | 35.2 | 70.4 | 28.9 |

Out of the results for the % hydrolysis it can be calculated that for feed B (MCTG2 and C (MCTG2+L5) respectively, 0.3 and 0.4% free MCFA are present in the stomach. In the experiment with the cannulated pigs the highest concentrations of free MCFA (and the strongest inhibition of the bacterial load, ±100 fold) were obtained with MCTG1+L5 and coconut oil+L5, 0.60 and 0.30% respectively.

The combined results of experiment 2 and 3 clearly indicate that there is a correlation between the amount of released free MCFA and the inhibitory effect on the gastric flora.

Experiment 4

In Vitro Evaluation of the Optimal Combination of Different Concentrations of MCTG with Different Doses of a Selected Lipolytic Enzyme.

Because it is our opinion that growth promotion is related and proportional to the inhibition of the total bacterial load in the small intestine, the following in vitro experiment, in which an ± optimal combination of the content of a MCFA containing TG (MCTG1, MCTG2 and coconut oil) and a proven effective lipase (L5) was set up.

Four concentrations TG were used: 0, 2.5, 5 and 10%; for each concentration TG, the lipase (15) was incorporated at 10,000, 1000, or 100 ppm. The medium contained also 2.5 g per incubation flask of the same synthetic fee (based on starch, dextrose, casein and vitamin-mineral premix) as used in experiment 1. However in present experiment the TG was dispersed (using gum Arabic and gum tragacanth) before adding to the medium. The incubations were done at pH 5 using an appropriate acetate buffer. Finally the medium (15 ml) was inoculated with 1 ml of a suspension of bacteria originating from the ileal contents of two canulated pigs fed a diet without growth promoting additives. Incubations were done for 180 min at 37° C. in a shaking water bath. All incubations were done in duplo.

The methods for the analysis of fats and the bacterial counts were the same as used in previous experiments. Only the total anaerobic count is reported here. Because a relationship between the antibacterial activity and the moleculair weight of the FA was expected, the results for the free fatty acids were also expressed on a molar basis. The results are given in table 9.

TABLE 9

Relationship between the in vitro release of free fatty acids (g% or moles in the medium) and the total anaerobic count ($\log_{10}$ CFU/ml medium) with different TG's (MCTG1, MCTG2 and coconut oil) and different doses (10,000, 1000 and 100 ppm) of a lipolytic enzyme (L5)

| | free FA g% | free FA M | total count $\log_{10}$ CFU/ml |
|---|---|---|---|
| MCTG1 | | | |
| Start | 0 | 0 | 6.2 |
| 180 min, control | 0 | 0 | 6.8 |
| 180 min, 10,000 ppm L5 | | | |
| 2.5% MCTG1 | 0.17 | 0.012 | 5.9 |
| 5% MCTG1 | 0.34 | 0.024 | <1 |
| 10% MCTG1 | 0.63 | 0.044 | <1 |
| 180 min, 1000 ppm L5 | | | |
| 2.5% MCTG1 | 0.11 | 0.008 | 6.1 |
| 5% MCTG1 | 0.20 | 0.014 | 4.8 |
| 10% MCTG1 | 0.39 | 0.027 | 3.8 |
| 180 min, 100 ppm L5 | | | |
| 2.5% MCTG1 | 0.09 | 0.006 | 6.5 |
| 5% MCTG1 | 0.13 | 0.009 | 6.5 |
| 10% MCTG1 | 0.22 | 0.015 | 6.2 |
| MCTG2 | | | |
| Start | 0 | 0 | 6.3 |
| 180 min, control | 0 | 0 | 7.0 |
| 180 min, 10,000 ppm L5 | | | |
| 2.5% MCTG2 | 0.17 | 0.012 | 5.5 |
| 5% MCTG2 | 0.30 | 0.021 | 3.4 |
| 10% MCTG2 | 0.58 | 0.040 | 1.8 |
| 180 min, 1000 ppm L5 | | | |
| 2.5% MCTG2 | 0.13 | 0.009 | 6.3 |
| 5% MCTG2 | 0.21 | 0.015 | 6.3 |
| 10% MCTG2 | 0.36 | 0.025 | 5.6 |
| 180 min, 100 ppm L5 | | | |
| 2.5% MCTG2 | 0.11 | 0.008 | 6.5 |
| 5% MCTG2 | 0.16 | 0.011 | 6.6 |
| 10% MCTG2 | 0.23 | 0.016 | 6.7 |
| COCONUT OIL | | | |
| start | 0 | 0 | 6.3 |
| 180 min, control | 0 | 0 | 7.1 |
| 180 min, 10,000 ppm L5 | | | |
| 2.5% coc. oil | 0.10 | 0.007 | 7.2 |
| 5% coc. oil | 0.16 | 0.011 | 6.2 |
| 10% coc. oil | 0.36 | 0.025 | 6.2 |
| 180 min, 1000 ppm L5 | | | |
| 2.5% coc. oil | 0.07 | 0.005 | 6.4 |
| 5% coc. oil | 0.13 | 0.009 | 6.5 |
| 10% coc. oil | 0.22 | 0.015 | 6.4 |
| 180 min, 100 ppm L5 | | | |
| 2.5% coc. oil | 0.05 | 0.003 | 6.9 |
| 5% coc. oil | 0.08 | 0.006 | 7.0 |
| 10% coc. oil | 0.13 | 0.009 | 7.0 |

The results can be summarized as follows

The amount of released FA is nearly proportional to the concentration of the TG, while a 10 fold increase of the dosis of the lipolytic enzyme used only doubled the concentration of the free FA. For each combination of a % TG and a given ppm lipolytic enzyme the release of FA follows the order: MCTG1>MCTG2>coconut oil.

The higher the concentration of the free FA, the more pronounced the suppression of the number of bacteria. A minimal concentration of ±0.35 g % FA the medium looks necessary for a significant suppression of the flora; this corresponds with 0.025 M/liter. The order MCTG1>MCTG2>coconut oil corresponds with an increase of the moleculair weight of the quantitatively most important MCFA in the TG: MCTG1 CB, MCTG2=C10, coconut oil=C12.

The used in vitro protocol offers an excellent tool for the screening of the numerous combinations of MCFA containing TG's and available lipolytic enzymes for their usefulness as feed supplements with a stabilizing or suppressive effect on the gastrointestinal microflora. This effect is generally accepted as the basis for obtaining a growth promotion.

TABLE 10

Examples of commercial sources of chemically synthesized structured lipids (1)

| Product | Composition | Company |
|---|---|---|
| Aldo MCT | C8, C10 | Lonza Inc., Fair Lawn, USA |
| Stabilox-860 | C8, C10 | Loders-Croklaan BV, Wormerveer, NL |
| Caprenin | C6:0, C8:0, C22:0 | Proctor & Gamble, Cincinatti, OH: |
| Salatrim | C3:0, C4:0, C18:0 | Nabisco Foods Group, East Hanover, NJ |
| Captex | C8:0, C10:0, C18:2 | Abitec, Columbus, OH |
| Captex 300 | C8, C10 | Capital City Products, Columbus, OH |
| Captex 810B | C8, C18 | Capital City Products, Columbus, OH |
| Tripelargonate | C9 | Capital City Products, Columbus, OH |
| Mixed odd chain | C7, C9 | Abbott Laboratories, North Chicago, IL |
| Neobee | C8:0, C10:0, LCFA | Stepan Co, Maywood, NJ |
| Neobee M5 | C8:0, C10:0 | Stepan Co, Maywood, NJ |
| Neobee 1095 | C10:0 | Stepan Co, Maywood, NJ |
| Coconado | C8:0 | Kao Co, Wakayama, Japan |
| Coconard-RK | C8, C10, C12 | Kao Co, Wakayama, Japan |
| MCTG | C4, C5, C6, C7, C8, C10 | Karlshamns Lipid Specialties, Columbus, OH |
| MCTG | C8, C10 | Mead Johnson & Co, Evansville, IN |

(1) source: tested products + literature compilation

TABLE 11

Examples of experimental or commercially available microbial lipases (1)

| Origin | Organism | Company |
| --- | --- | --- |
| Yeast | *Candida* sp. | |
| | *Candida rugosa** | Amano, Biocatalysts, Boehringer Mannheim Fluka, Genzyme, Sigma, Meito Sankyo |
| | *Candida antartica* A/B | Boehringer Mannheim, Novo Nordisk |
| | *Candida lipolytica* | |
| | *Candida paralipolytica* | |
| | *Saccharomyces lipolytica* | |
| Fungal | *Thermomyces lanuginosus*** | Novo Nordisk, Boehringer Mannheim, Amano |
| | *Rhizomucor Miehei* | Novo Nordisk, Biocatalysts, Amano |
| | *Rhizopus* sp. | Nagase, Tokyo, Japan |
| | *Rhizopus delemar* | |
| | *Rhizopus oryzae* | |
| | *Rhizopus niveus* | Alltech, |
| | *Rhizopus arrhizus* | Sigma |
| | *Rhizopus javanicus* | Amano |
| | *Aspergillus* sp. | |
| | *Aspergillus niger* | Finnfeeds International, Amano |
| | *Aspergillus usamii* | |
| | *Aspergillus oryzae* | Novo Nordisk |
| | *Mucor* sp. | |
| | *Mucor javanicus* | |
| | *Mucor lipolyticus* | |
| | *Penicillium* sp. | |
| | *Penicillium roquefortii* | Amano |
| | *Penicillium cyclopium* | Amano |
| | *Penicillium simplissimum* | |
| | *Penicillium camembertii* | |
| | *Geotrichum candidum* | Amano |
| | *Neurospora crassa* | |
| | *Ustilago maydis* | |
| | *Fusarium solani* | |
| Bacterial | *Burkholderia cepacia**** | Amano, Fluka, Boehringer Mannheim |
| | *Pseudomonas* sp. | |
| | *Pseudomonas alcaligenes* | Genencor |
| | *Pseudomonas mendocina* | Genencor |
| | *Pseudomonas fluorescens* | |
| | *Pseudomonas aeroginosa* | Amano |
| | *Pseudomonas* spp. | Finnfeeds International; Karlan, CA, USA |
| | *Chromobacterium viscosum***** | Asahi, Tokyo, Japan; Biocatalysts; Karlan, CA, USA; Toyo Jozo Shizuoka, Japan |
| | *Staphylococcus* sp. | |
| | *Staphylococcus aureus* | |
| | *Staphylococcus carnosus* | |
| | *Staphylococcus hyicus* | |
| | *Achromobacter lipolyticum* | |
| | *Acinetobacter* | |
| | *Propionibacterium acnes* | |
| | *Bacillus* sp. | |

*formerly named *Candida cylindracea*
**formerly named *Humicola lanuginosus*
***formerly named *Pseudomas cepacia*
*****C. viscosum* is identical to *Burkholderia glumae*
(1) source: tested products + literature compilation

REFERENCES

Bach, A. C. & Babayan, V. K., 1982, Medium-chain Triglycerides: an Update, The American Journal of Clinical Nutrition, 36: 950-962

Cera, K. R. et al., 1989, Postweaning Swine Performance and Serum Profile Responses to Supplemented Medium-chain Free Fatty Acids and Tallow, Journal of Animal to Science, 67, 2048-2055

Chesson, A., 1994, Probiotics and other Intestinal Mediators, In: Principles of Pig Science, D. J. A. Cole, J. Wiseman & M. A. Varley, Editors, Nottingham University Press, UK, pp. 197-214

Corpet, D. E., 1996, Microbial Hazards for Humans of Antimicrobial Growth Promotor Use in Animal Production, Revue Médicine Vétérinaire, 147:851-862

Decuypere, J. A. et al., 1977, Gastro-intestinal Cannulation in Pigs: a Simple Technique allowing multiple Replacements, Journal of Animal Science, 46, 463-468

Kabara, J. J., 1978, Fatty Acids and Derivates as Antimicrobial Agents—a Review, In: The Pharmacological Effects of Lipids, J. J. Kabara, Editor, The American Oil Chemists Association, Champaign, II, USA, pp. 1-14

Odle, J., 1999, Medium-chain Triglycerides: a Unique Energy Source for Neonatal Pigs, Pig News and Information, 20: 25N-32N Lepine, A. J. et al., 1989, Effect of Colostrum or Medium-chain Triglyceride Supplementation on the Pattern of Plasma Glucose, Non-esterified Fatty Acids and Survival of Neonatal Pigs, Journal of Animal Science, 67, 983-990

Moreau, H. et al., 1988, Screening of Preduodenal Lipases in several Mammals, Biochemica Et Biophysica Acta, 959, 247-252

Partridge, G. G., 1993, New Approaches with Pig Weaner Diets, In: Recent Advances in Animal Nutrition, P. C. Gansworthy & Cole, .J. A., Editors, Nottingham University Press, UK, pp. 221-248

Roth, F. X. & Kirchgessner, 1998, Organic Acids as Feed Additives for young Pigs: Nutritional and Gastrointestinal Effects, Journal of Animal and Feed Sciences, 7: 23-33

SPSS for WINDOWS, 1997, Users Guide (Release 7.5), SPSS Inc., Chocogo, Ill. 60611

Van der Heyde, H. & Henderickx, H., 1963, Zur Vereinfachung der quantitativen und qualitativen Bestimmung der Bakterien unter Verwendung von "Ringplatten", Zentralblatt Für Bakteriologie, I Orig., 189, 224-228

Van der Peet, G. F. V., 1992, Voeding van jonge Biggen, CVB-Documentatierapport N°5

Wegener, H. C. et al., 1998, The Association between the Use of Antimicrobial Growth Promoters and Development of Resistance in Pathogenic Bacteria towards Growth Promoting and Therapeutic Antimicrobials, Journal of Animal and Feed Science, 7: 7-14

The invention claimed is:

1. A feed composition comprising an animal feed, about 2.5% to about 10% by weight of triglycerides containing $C_4$-$C_{12}$ medium chain fatty acids and about 1,000 ppm to about 10,000 ppm of exogenous active lipolytic enzyme.

2. The feed composition according to claim 1 for use as an antimicrobial agent.

3. The feed composition according to claim 1 for preventing digestive upsets.

4. The feed composition according to claim 1, wherein said exogenous active lipolytic enzyme is a lipase.

5. The feed composition according to claim 1, wherein said exogenous active lipolytic enzyme is an esterase.

6. The feed composition according to claim 1, wherein said exogenous active lipolytic enzyme is a mixture of lipase and esterase.

7. The feed composition according to claim 1 for feeding early weaned piglets.

8. The feed composition according to claim 1, wherein said triglycerides consist of $C_6$-$C_{12}$ medium chain fatty acids.

9. The feed composition according to claim 1, wherein said animal feed comprises starch, dextrose, casein and a vitamin-mineral premix.

10. The feed composition according to claim 1, wherein said animal feed comprises maize, barley, wheat, dried acid whey, cassava, herring meal, soybean, soy-flour and a vitamin-mineral premix.

* * * * *